United States Patent [19]

Blankenhorn

[11] Patent Number: 4,726,673
[45] Date of Patent: Feb. 23, 1988

[54] TACHISTOSCOPE FOR PRESENTING STIMULI IN LATERALIZED FORM

[75] Inventor: David H. Blankenhorn, Pasadena, Calif.

[73] Assignee: University of Southern California, Los Angeles, Calif.

[21] Appl. No.: 859,556

[22] Filed: May 5, 1986

[51] Int. Cl.[4] .................... G02B 27/02; A61B 3/00
[52] U.S. Cl. .................................................. 351/238
[58] Field of Search ............... 351/238, 239, 240, 232

[56] References Cited

U.S. PATENT DOCUMENTS

| 1,662,054 | 7/1926 | Beall | 351/239 |
| 2,196,904 | 4/1940 | Sherman | 351/240 |
| 3,837,734 | 9/1974 | Regan | 351/232 |

Primary Examiner—Bruce Y. Arnold
Assistant Examiner—Kevin Fournier
Attorney, Agent, or Firm—Nilsson, Robbins, Dalgarn, Berliner, Carson & Wurst

[57] ABSTRACT

A tachistoscope system is presented in which separate images may be sent to the left and right hemispheres of the visual cortex. A subject-worn viewing system having electro-optical valves is used to cover the right and left visual fields of the subject and the valves are operable in response to control signals. These control signals also synchronize the inputs from 2 television cameras with the opening of the valves. An alternative embodiment employs lenses of different colors arranged to cover the right and left visual fields of the subject and means for displaying colored areas of output.

14 Claims, 5 Drawing Figures

TACHISTOSCOPE FOR PRESENTING STIMULI IN LATERALIZED FORM

BACKGROUND OF THE INVENTION

1. Field of the Invention

This invention relates to systems for presenting visual stimuli often referred to as tachistoscopes. More particularly, this invention relates to systems for selectively lateralizing the input of visual stimuli by occluding parts of the visual field and thereby separately stimulating the different hemispheres of the cortex.

2. State of the Art

Recent studies have revealed specializations in the functions of the right and left cerebral hemispheres of the cortex. It has therefore become important to separately study and train the cerebral hemispheres. This may be accomplished by selectively applying visual stimuli to different areas of the occular retinas since the left and right sides of the retinas are coupled to different hemispheres of the cortex. Consequently, by occluding vision from one side of a retina and thereby presenting stimuli in a lateralized form the right and left hemispheres of the visual cortex may be separately (hemianoptically) stimulated.

In the past, study and training through hemianoptical stimulation have been effected by the use of mechanical shutter devices which present information to subjects who would sit with their heads clamped in a stable position watching a central fixation point. However, with this technique, information can only be presented for short periods before naturally occurring eye movements alter the visual field of the subject. Alternatively, contact lenses of special construction have been used to achieve hemianoptic stimulation. These lenses are covered with opaque material except for vertical slits decentered from the optical axis or they are attached to collimator assemblies including caps for occluding the visual field. However, these devices are uncomfortable for many subjects to use and do not allow for simultaneous stimulation of both hemispheres.

The present invention helps to overcome the aforementioned limitations by providing a system for hemianoptical visual stimulation which is effective yet easy to utilize, allows complex and rapidly changing images to be presented, permits extended exposure periods to stimuli, and provides for effectively simultaneous stimulation of both hemispheres with different stimuli.

SUMMARY OF THE INVENTION

The present invention constitutes an apparatus and resulting method for presenting visual stimuli in lateralized form to a subject viewing a series of images. The apparatus includes means for displaying different visual outputs at different times in response to control signals, a subject-worn viewing system having electrooptical valves which are arranged to cover the right and left visual fields of the subject and are operable in response to control signals and means for providing signals for controlling the display means and the viewing system. In operation, the viewing system and the display means are driven in synchrony by the control means so that different visual outputs are presented to the right and left visual fields of the viewer thereby effecting hemianoptical stimulation.

In an alternative embodiment of the present invention a subject-worn viewing system employs lenses of different colors arranged to cover the right and left visual fields of the subject and means for displaying colored areas of output. In this embodiment the output of the display means is hemianoptically viewed depending on the color combination of output and the lenses.

DESCRIPTION OF THE PREFERRED EMBODIMENT

Figure 1:
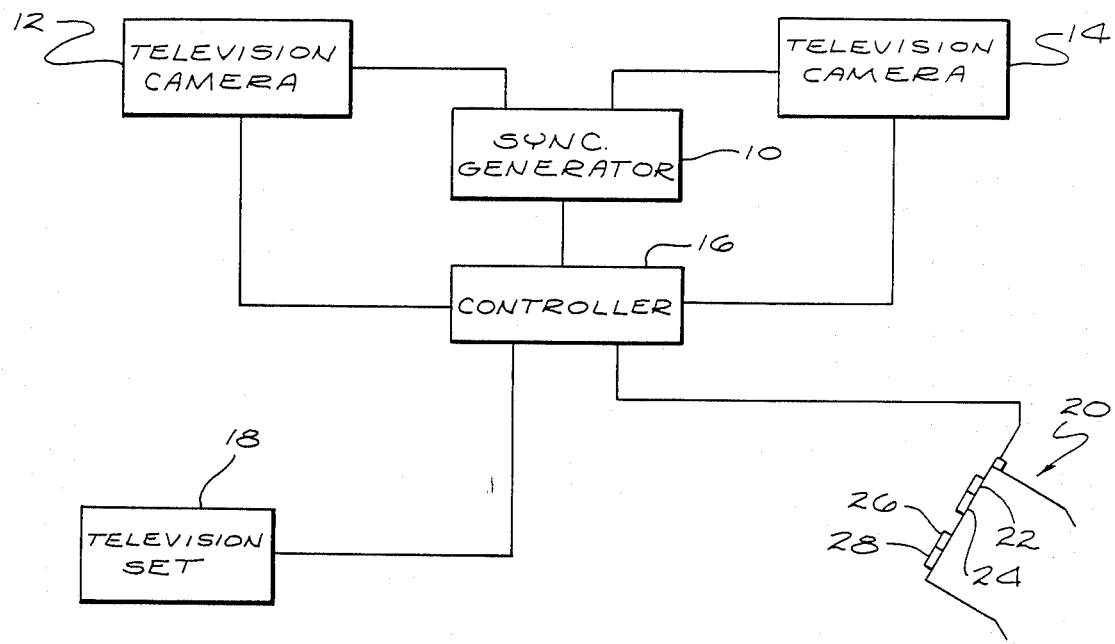
FIG. 1 is a block diagram showing the major components of the system of the invention.

Referring to FIG. 1, the major components of the system 11 of the present invention are illustrated. A synchronization generator 10 is electrically connected to two television cameras 12 and 14 as well as a controller 16. The generator 10 provides synchronization signals including odd and even field signals to govern the operation of the cameras 12 and 14. The same synchronization signals are also provided to the controller 16 for use in timing the overall operation of the system. The television cameras 12 and 14 are also connected to the controller 16 and the video outputs of the cameras 12 and 14 are thereby supplied to the controller. Additionally, the controller 16 is electrically connected to the television set 18 and to the viewing system 20. The controller 16 receives the field synchronization signals provided by the generator 10 and selectively transmits the video output of the camera 12 to the set 18 for odd field signals and selectively transmits the video output of the camera 14 to the set 18 for even field signals. Based on the field synchronization signals supplied by the generator 10, the controller 16 also selectively provides operating signals to the electro-optical valves 22, 24, 26 and 28 of the viewing system 20 as will be further described hereinafter.

The controller 16 and viewing system 20 of the present invention bear similarity to the shutter control and stereoscopic analyzer components of the invention described in U.S. Pat. No. 3,821,466 to Roese and the transmission means and display means described in U.S. Pat. No. 4,214,267 to Roese, which patents are hereby incorporated herein by reference.

Figure 2:
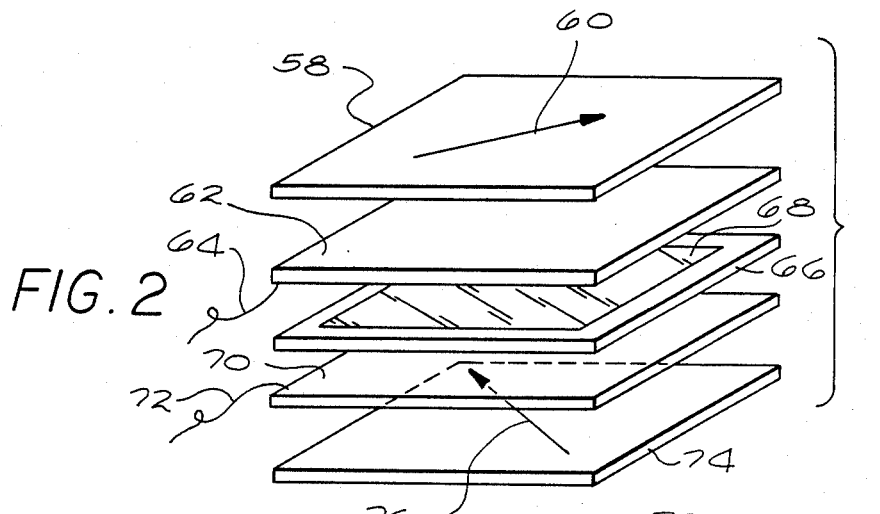
FIG. 2 is an exploded view of one of the electro-optical valve assemblies used in the subject-worn viewing system in accordance with the invention.

Referring now to FIG. 2, a viewing system 20 suitable for being worn by a test subject is shown in the form of a set of specially constructed eyeglasses nevertheless having a conventional front frame 30 in which lenses may be mounted and temple pieces 32 which provide positional support. A web 34 of an opaque material may be additionally added to block out light from peripheral sources.

In place of the lenses used in conventional eyeglasses, the electro-optical valves 22, 24, 26 and 28 are mounted in frame 33. The valves 22 and 24 are arranged side by side so that the centerline of their common junction 36 coincides with the front vertical optical axis of the right eye of the subject. The valves 26 and 28 are arranged side by side so that the centerline of their common junction 38 coincides with the front vertical optical axis of the left eye of the subject. Both junctions 36 and 38 include spacers 40 and 42 which may be of varying sizes according to the application and which separate the optical valves and block vision corresponding to a strip down the center of the retina of each eye. The spacers 40 and 42 help to maintain the right and left visual fields separate and prevent images intended for one side of the visual field from being partially viewed on the other side due to variations in the direction of focus of the eyes of the subject.

A lightweight cable 44 electrically connects the controller 16 to the valves 22, 24, 26 and 28 of the system 20. The electrical leads 46, 48, 50 and 52 from cable 44 connect through the electrical junction 54 to the valves 22, 24, 26 and 28, while the ground lead 56 connects to all four valves.

Figure 3:
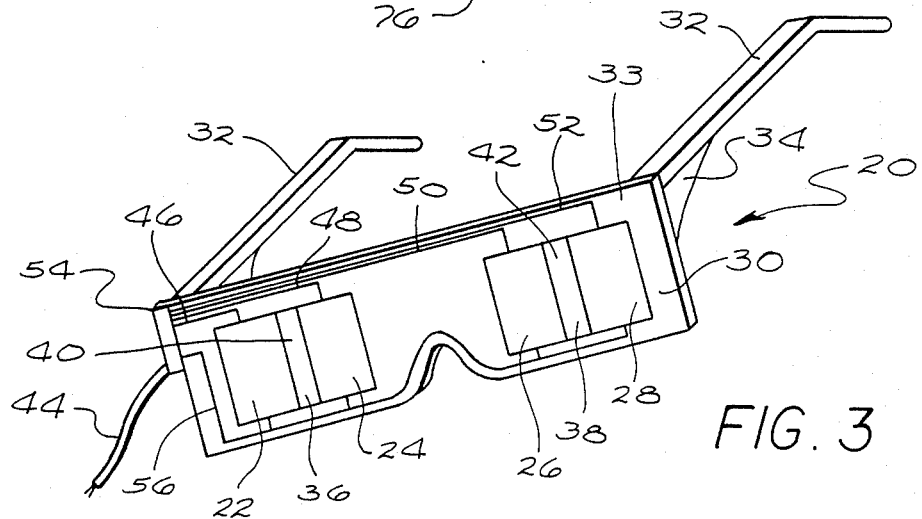
FIG. 3 is a perspective view of the viewing system according to the invention.

Referring now to FIG. 3 an electro-optical assembly of the type which may be used for the valves 22, 24, 26 or 28 is illustrated. The assembly has a front polarizer 58 having an axis of polarization as shown by the arrow 60. The next element is a glass plate 62 having a transparent conductive coating on the bottom thereof connected to an electrical lead 64. The middle element is a spacer 66 which includes a well 68 in which a nematic liquid crystal material is disposed. The spacer 66 is followed by another glass plate 70 having a transparent conductive coating on the top thereof connected to an electrical lead 72. The bottom element is a polarizer 74 having an axis of polarization as shown by the arrow 76, which is perpendicular to the axis of polarization of the polarizer 58.

In the absence of a voltage between the leads 64 and 72, and therefore across the plates 62 and 70, the assembly is opaqued due to the action of polarizers 58 and 74 in blocking light. When a voltage of approximately eight volts is applied across the plates 62 and 70, the liquid crystal material rotates the plane of polarization of light passing therethrough by approximately ninety degrees such that light passing through the polarizer 58 may also pass through the polarizer 74 and the assembly is effectively transparent.

Since the operation of the television set 18 and the viewing system 20 are controlled in accordance with the same signals (the field synchronization signals from the generator 10), their operation is coordinated as shown in the following Table I:

TABLE I

| | TIME 1 | TIME 2 |
|---|---|---|
| Field Signal | ODD | EVEN |
| Output to Monitor | LEFT CAMERA | RIGHT CAMERA |
| Valves Open | LEFT VALVE OF EACH VALVE PAIR | RIGHT VALVE OF EACH VALVE PAIR |
| Hemispherical Cortex Stimulated | LEFT VISUAL | RIGHT VISUAL |

In accordance with the above, the left hemispherical cortex is separately stimulated by images from the left camera and the right hemispherical cortex is separately stimulated by images from the right camera.

The system may, however, be further refined by varying the brightness of the images or the number of images provided by each camera to adjust the amounts of stimulation presented to the subject and provide different amounts of stimulation to each hemisphere or accommodate variations in the relative performance of the two hemispheres.

Figure 4:
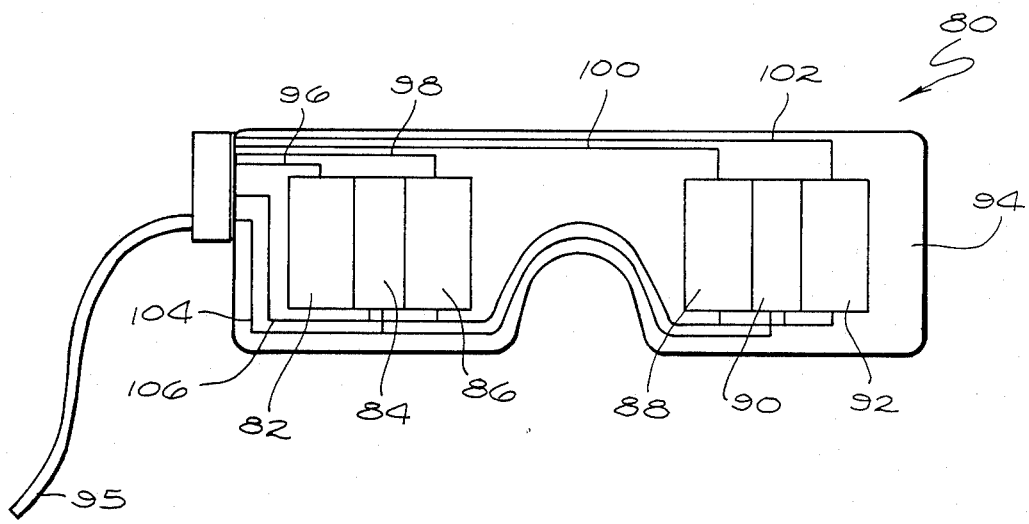
FIG. 4 is a front view of an alternative type of viewing system in accordance with the present invention.

Referring now to FIG. 4, an alternative viewing system 80 is illustrated. The viewing system 80 is similar to the viewing system 20 except that six electro-optical valves 82, 84, 86, 88, 90 and 92 are mounted in the frame 94. The valves 82, 84 and 86 are arranged side by side as a set with the valve 84 between the valves 82 and 86. The centerline of the valve 84 coincides with the front vertical optical axis of the right eye of the subject so that the valves 82, 84 and 86 cover the left, center and right visual fields of the subject. The valves 88, 90 and 92 are arranged side by side as a set with the valve 90 between the valves 88 and 92. The centerline of the valve 90 coincides with the front vertical optical axis of the left eye of the subject so that the valves 88, 90 and 92 cover the left, center and right visual fields of the subject. The central valves 84 and 90 may be of various shapes and sizes such as oval depending on the area of central vision which is determined to be optimum for each application and each subject. A lightweight cable 95 electrically connects the controller 16 to the valves 82, 84, 86, 88, 90 and 92 of the system 80. The electrical leads 96, 98, 100, 102, from the cable 44 connect through the junction box 108 to the valves 82, 86, 88 and 92, respectively. The electrical lead 104 connects to the valves 84 and 90, while the ground lead 106 connects to all six valves.

In this alternative system, an additional video output is provided to controller 16 by a third video camera. The controller 16 then transmits the additional video output to the television set 18 for an entire frame after every four fields (two frames) of output from the cameras 12 and 14. The controller 16 selectively provides operating signals to the viewing system 20 so that the operation of the television set and viewing system are coordinated as shown in the following Table II:

TABLE II

| Time of Occurrence | EVERY 1ST & 2ND FRAME | EVERY 1ST & 2ND FRAME | EVERY 3RD FRAME |
|---|---|---|---|
| Field Signal | ODD | EVEN | ODD & EVEN |
| Output to Monitor | LEFT CAMERA | RIGHT CAMERA | 3RD CAMERA |
| Valves Open | LEFT VALVE OF EACH VALVE SET | RIGHT VALVE OF EACH VALVE SET | CENTER VALVE OF EACH VALVE SET |
| Cortex Stimulated | LEFT VISUAL | RIGHT VISUAL | (BOTH, FOCUSING INFO. ONLY) |

In accordance with the above, the left and right hemispherical cortexes are respectively stimulated. However, upon the occurrence of every third frame, the viewer is allowed combined vision with both the left and right visual fields of each eye through the vertical apertures defined by the central valves to faciliate accurate focusing. In general, no useful information would be displayed to the viewer during the third frame except a focusing image such as a single vertical stripe in the center of the screen of the television set 18. Nevertheless, useful information may be displayed during the focusing period if it is desired to separately study or train one or both hemispheres concurrently with the combined visual cortex.

Figure 5:
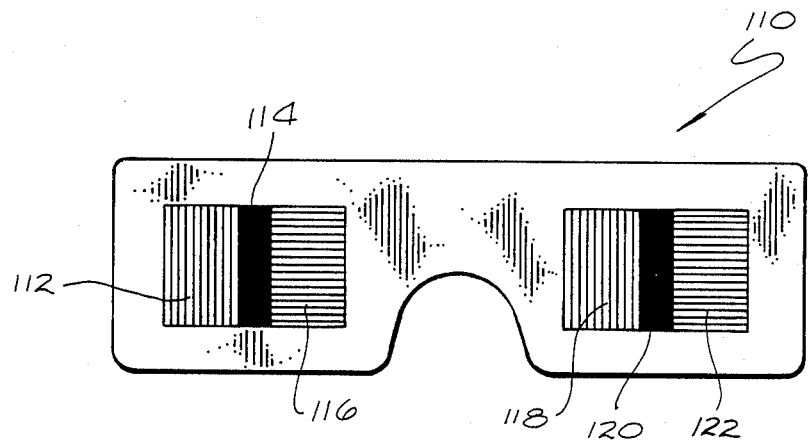
FIG. 5 is a front view of an alternative embodiment of the present invention.

Referring now to FIG. 5, a viewing system 110 for use in an alternative embodiment of the present invention is illustrated. The viewing system 110 comprises a conventional pair of eyeglasses having specially colored lenses 112, 114, 116, 118, 120 and 122 mounted side by side in the front of the frame 124. The lenses 112, 114 and 116 are arranged as a set with the lens 114 between the lenses 112 and 116. The centerline of the lens 114 coincides with the front vertical optical axis of the right eye of the subject so that the lenses 112, 114 and 116 cover the left, center and right visual fields of the subject. The lenses 118, 120 and 122 are arranged as a set with the lens 120 between the lenses 118 and 122. The centerline of the lens 120 coincides with the front vertical optical axis of the left eye of the subject so that the lenses 118, 120 and 122 cover the left, center and right visual fields of the subject. The lenses 112 and 118 are red colored and the lenses 116 and 122 are blue colored. The colors of the lenses are chosen so that the different sets of lenses covering each visual field will transmit mutually exclusive images. The lenses for each visual field will allow transmission of one colored image and block all images of a different color which are transmitted by any of the other sets of lenses. The lenses 114 and 120 are colored black so as to block out light and help maintain the right and left visual fields separate although the lenses 114 and 120 could be colored green and used for other purposes such a to promote focusing. The viewing system 110 is used in conjunction with a screen on which colored images are projected.

In operation, red images are viewed by a subject through the red lenses 112 and 118 by the right visual cortex while their transmission is blocked by the blue lenses 116 and 122. Blue images are viewed by the subject through the blue lenses 116 and 122 by the left visual cortex while their transmission is blocked by the red lenses. Therefore, by sequentially projecting different red and blue images on a screen being viewed by the subject hemianoptical stimulation may be achieved.

While the system of this invention has been described in conjunction with the above embodiments, it should be apparent that changes can be made without departing from the principles of the invention. For example, the video cameras 12 and 14 can be replaced by other means for providing video outputs such as video tape recorders, video cassette recorders, the foregoing utilizing magnetic storage media, video disk systems or computer based image generation systems. Also, synchronization generators can be built into the cameras 12 or 14 with the operation of one camera then locked to the synchronization signal provided by the other. Additionally, the electro-optical valves 22, 24, 26 and 28 can alternatively comprise lanthanum modified lead zirconate-titanate (PLZT) light valves. Further, the controller 16 can regulate the television set 18 and the viewing system 20 based on signals other than the field synchronization signal so that entire frames of video output or sets of frames of such output may be separately presented to each hemispherical cortex. Additionally, lateralized auditory or tactile stimulation may be presented in synchrony with lateralized visual stimulation. Consequently, the descriptions provided are intended as illustrative only and are not meant to limit the scope of the claims.

What is claimed is:

1. An apparatus for presenting visual stimuli in lateralized form to a viewer, which comprises:
   means for displaying different visual outputs at different times;
   a viewing system having a plurality of light valves arranged to cover the left and right visual fields of the viewer; and
   means for controlling the display of the visual outputs and the operation of the viewing system so that the outputs are displayed and the valves are operated in synchrony,
   whereby different images may be presented to the left sides and right sides of the retinas of the viewer resulting in hemianoptical stimulation.

2. The apparatus of claim 1 wherein the visual outputs are video outputs and the light valves are electro-optical light valves.

3. An apparatus for presenting visual stimuli in lateralized form, which comprises:
   means for generating video synchronization signals;
   means for supplying two different video outputs in accordance with said synchronization signals;
   a television set for displaying video outputs;
   a viewing system having a plurality of electro-optical light valves arranged to cover the left and right visual fields of the viewer, the valves operable in response to electrical control signals; and
   controller means for transmitting different video outputs to the television set and providing different control signals to the light valves based on the synchronization signals so that the valves are driven in synchrony with the different video outputs,
   whereby different images may be separately presented to the left sides and right sides of the retinas of the viewer resulting in hemianoptical stimulation.

4. The apparatus of claim 3 wherein the means for supplying two different video outputs comprises two video cameras.

5. The apparatus of claim 3 wherein the means for supplying two different video outputs utilizes magnetic storage media.

6. The apparatus of claim 3 wherein the means for supplying two different video outputs comprises two computer-based image generation systems.

7. The apparatus of claim 3, wherein the viewing system also includes two thin spacers separating the optical light valves covering the right and left visual fields of each eye of the viewer.

8. An apparatus for presenting visual stimuli in lateralized form, which comprises:
   means for generating video synchronization signals;
   video camera means for supplying two different video outputs in accordance with the synchronization signals;
   a television set for displaying video outputs;
   a viewing system having four electro-optical light valves arranged to cover the right and left visual fields of the viewer and two spacers for separating the valves covering the different visual fields of each eye, the valves operable in response to electrical control signals; and a controller for transmitting different video outputs to the television set and providing different control signals to the light valves so that the valves are driven in synchrony with the different video outputs, whereby different images may be separately presented to the left sides and right sides of the retinas of the viewer resulting in hemianoptical stimulation.

9. A method for accomplishing hemianoptical stimulation of a subject viewing visual outputs, comprising the steps of:

displaying two different visual outputs to the viewer at different times; and operating a viewing system, including a plurality of light valves arranged to cover the left and right visual fields of the subject, in synchrony with the display of the visual outputs so that different outputs are presented to different sides of the retinas of the subject.

10. A method for accomplishing hemianoptical stimulation of a subject viewing a television set, comprising the steps of:

providing a video synchronization signal for governing the operation of means for supplying two different video outputs;

supplying two different video outputs governed in accordance with the synchronization signal;

displaying the different video outputs on the television set at different times;

operating a viewing system, including a plurality of electro-optical valves arranged so as to cover the left and right visual fields of a viewer; and regulating the display of the video outputs on the television set and the operation of the valves of the viewing system so that the television set and viewing system are driven in synchrony based on the synchronization signal, whereby different video outputs are presented to the right and left fields of vision of each eye of the viewer and visual stimuli are presented in a lateralized form to the viewer.

11. An apparatus for presenting visual stimuli in lateralized form, which comprises:

means for generating video synchronization signals;

means for supplying three different video outputs in accordance with said synchronization signals;

a television set for displaying video outputs;

a viewing system having a plurality of electro-optical light valves arranged to cover the left, right and center visual fields of the viewer, the valves operable in response to electrical control signals; and controller means for transmitting different video outputs to the television set and providing different control signals to the light valves based on the synchronization signals so that the valves are driven in synchrony with the different video outputs, whereby different images may be separately presented to the left and right sides and center area of the retinas of the viewer resulting in hemianoptical stimulation.

12. An apparatus for presenting visual stimuli in lateralized form, which comprises:

a viewing system having a plurality of different sets of colored lenses which are adapted for transmitting colored images on a mutually exclusive basis and are arranged to cover different visual fields of the viewer so that each visual field is viewed by the subject through lenses of a separate color;

means for sequentially displaying different colored images suitable for being transmitted by said sets of lenses on a mutually exclusive basis.

13. The apparatus of claim 12, wherein said viewing system includes two sets of different colored lenses, the colors of which are chosen from the group consisting of red, blue and green.

14. A method for accomplishing hemianoptical stimulation of a subject viewing visual images, comprising the steps of:

arranging sets of lenses having different colors adapted for viewing images having different colors on a mutually exclusive basis so that the sets cover different visual fields of the subject corresponding to the left and right visual cortexes of the subject;

displaying to the subject at different times different visual images having different colors which may be viewed through colored lenses on a mutually exclusive basis.

* * * * *